(12) United States Patent
De Luca

(10) Patent No.: US 6,224,371 B1
(45) Date of Patent: May 1, 2001

(54) SUPPORTING DEVICE FOR THE MANUFACTURE OF DENTAL PROSTHETIC COMPONENTS

(76) Inventor: Silvio De Luca, Rua General Artigas, 119 - Leblon, Rio de Janeiro - RJ 22450-010 (BR)

( * ) Notice: Subject to any disclaimer, the term of this patent is extended or adjusted under 35 U.S.C. 154(b) by 0 days.

(21) Appl. No.: 09/285,661

(22) Filed: Apr. 5, 1999

(30) Foreign Application Priority Data

Dec. 29, 1998 (BR) .................................................... 9805906

(51) Int. Cl.[7] .................................................... A61C 8/00
(52) U.S. Cl. ................................................. 433/49; 264/19
(58) Field of Search .................................. 433/49, 50, 51, 433/201.1; 264/16, 19

(56) References Cited

U.S. PATENT DOCUMENTS

| | | | |
|---|---|---|---|
| 4,615,678 | * 10/1986 | Moermann et al. | 433/201.1 |
| 4,991,706 | * 2/1991 | Kitamura . | |
| 5,151,044 | * 9/1992 | Rotsaert | 433/229 |
| 5,342,696 | * 8/1994 | Eidenbenz et al. | 428/542.8 |
| 5,513,989 | * 5/1996 | Crisio | 433/176 |
| 5,775,911 | * 7/1998 | Hahn | 433/223 |
| 5,939,211 | * 8/1999 | Mörmann | 433/49 |

FOREIGN PATENT DOCUMENTS

| | | | |
|---|---|---|---|
| 3900695 | * 7/1990 | (DE) | 433/49 |

* cited by examiner

Primary Examiner—Ralph A. Lewis
(74) Attorney, Agent, or Firm—Finnegan, Henderson, Farabow, Garrett & Dunner, L.L.P.

(57) ABSTRACT

The invention proposes a supporting device for the manufacture of dental prosthetic components in the field of dental implants and, more specifically, of connecting elements, which provide a faster, cheaper and dependable technique, and which helps the dentist in his task with the objective of eliminating addition or subtraction operations when using said connection elements.

This objective is attained, in accordance with the invention, for the supporting device includes a support component (10) having an orifice (80) with an internal thread and a screw element with an external thread, which mutually engage to constitute a safe support for a machined odontological block to be formatted.

10 Claims, 2 Drawing Sheets

SUPPORTING DEVICE FOR THE MANUFACTURE OF DENTAL PROSTHETIC COMPONENTS

FIELD OF THE INVENTION

The present invention refers to a supporting device for the manufacture of dental prosthetic components and, more particularly, of connecting elements.

BACKGROUND OF THE INVENTION

Since the beginning of the eighties the odontology field has gone through a strong development in the field of implants with the advent of the root implants described by Branemark et al. This development allowed dentists to regularly execute surgeries, which until then were not so frequent, aiming to fix a implant part or piece in the maxillary or jawbone of a patient.

Indeed, the use of oral implants for the restoration of total or partial edentulism became a quite accepted practice in present odontology, as it allows the replacement of lost teeth with a corresponding dental prosthesis. This technique consists of a first surgical phase when a implant part is positioned inside the maxillary or jawbone, either in the form of a raw machined surface part or with the addition of biocompatible substances or by the subtraction of material, so as to perfectly integrate it to the receiving locus. In the case of addition one can employ, e.g., plasma spray, hydroxy apatite and other suitable materials, and, when subtracting, one can employ mechanical abrasion or acid attack techniques.

There are many known formats for the implant parts. Their basic structure, however, consists of a cylindrical wad or sleeve made of a special material, generally of noble and resistant materials, such as a titanium cylinder externally threaded in its lateral surface and with a passing axial internal channel, provided with an internal thread. During the surgical procedure, the patient maxillary or jawbone is perforated, and a implant part or cylindrical sleeve is firmly retained therein by means of the coupling of the external thread with the bone.

After the healing period determined by the dentist, dependent on the type of bone, the bone quality, etc., a second surgical procedure is effected for the positioning of a connecting element between the implant part, located inside the gum, and a crown body to be built. The term crown means the supra-gingival portion of the implant part or of a tooth.

After the second surgical procedure has healed, a mold is prepared for the manufacture of the patient buccal model, which is nothing but the faithful reproduction of the patient dental structure. During this step are taken the patient articulation registers or records; these are the records which shall determine the relative mutual position of both superior and inferior arcades.

With the models and registers it is then possible to proceed with the mounting on the articulation structure, with which begins the laboratory phase of rehabilitation.

During this laboratory phase it is determined the type of element to be used and the manufacture of the crown. The connecting element is in itself an union part between the implant part and the crown.

The presently available connecting elements exist in many forms; some are pre-fabricated, and over these one can position metallic or ceramic cylinders which will support the future crown; others consist of wax or plastic components, which are models manually sculptured by the prosthetic technician, which, after casting, can receive the future crown.

The connecting elements may consist, e.g., of a cylinder having a transfixing internal channel, coaxial with the cylinder geometric axis, said cylinder being fixedly coupled to the implant part already embedded in the maxillary or jawbone of the patient. The firm contact between the cylinder and the implant part is generally effected by means of a fastening threaded screw inserted within the cylinder internal channel, which cooperates with, or is threaded within, the internal thread of the internal threaded channel of the implant part.

The seating surface of the implant part may be provided with an anti-rotation means so as to prevent the rotary motion between the implant part and the connection element. This anti-rotation means may take the form of a hexagon, a Morse cone, or any other format. However, the presence of a anti-rotation means on the seating surface of the connection element is optional, as it is specific for each case.

When a anti-rotation means is used, it may consist, for example, of a projection or shoulder with an hexagonal form, or of a Morse cone, provided on the seating surface of the implant part, and of a corresponding recess provided in the seating surface of the connection element. When the connection element is positioned over the implant part, the projection on the implant part settles in the corresponding recess of the connection element and establishes a male-female type connection and prevents the relative rotation of these components. Over this support, formed and screwed as described, is positioned the crown itself, which may be screwed or cemented.

Presently, these connection elements are manufactured by specialized companies which adopt different manufacturing methods. They are supplied to the dentists in a standardized format, which has the inconvenience of not always adapt itself to the individual characteristics of each patient, specifically to the contour of the gum around the implant part, as this does not obey to an uniform format, demanding from the dentist, during the laboratory phase, the addition or subtraction of material to/from these connection elements. Besides the inherently high costs of the connection elements themselves, to the dentist labor are added all the other finishing operations of the connection element, implying in considerable costs in terms of working time.

Attempts to eliminate these problems, or to at least reduce the difficulties existing for the manufacturing of dental prosthetic components, have been effected by the manufacturing and supplying companies of connection elements, to reduce the angular problems which occur during the implant procedure, as the implant must surface from the tooth perimeter. Therefore, presently there already exist in the market connection elements having different configurations in the base portion and/or different angles at the cylindrical body. Even in these cases, however, a perfect adaptation to the specific anatomic details is not possible, in terms of the soft tissues anatomy of the patient and of the positioning of the implant in relation to the crown perimeter, remaining, however the above mentioned difficulties and disadvantages.

Therefore it is an object of the present invention to provide a supporting device for the manufacture of dental prosthetic components, of the above mentioned type, which shall eliminate the prior art difficulties and disadvantages described above, providing a faster, cheaper, and dependable method to manufacture connection elements.

Another object of the present invention is to help the dentist in his work, eliminating addition or subtraction operations to/from the connection elements, so as they can be manufactured in a fast and personalized form, at the dentist office, thereby avoiding the sculpturing phase.

SUMMARY OF THE INVENTION

The above mentioned objects are attained, in accordance with the present invention, through a supporting device for the manufacture of dental prosthetic components and, in particular, connecting elements, characterized in that it includes a support component having an orifice which includes first coupling means moveable along its longitudinal axis, and a fastening element, preferably made in the form of a head screw, having second coupling means, said fastening element being able to be able to be fastened and released to/from the support component through the cooperation between said first and second coupling means. In the present embodiment, the first coupling means preferably consist of an internal threaded portion on the orifice e the second coupling means consist of an external threaded portion on the shaft of the head screw.

The support component may be a whole, or one piece, part rotationally symmetrical, having a substantially discoid superior portion, and an inferior shaft portion. Conveniently, the discoid superior portion may include an antirotation means, built in the form of a projection on the seating surface, or of a similar cavity surrounding the orifice mouth.

In the present embodiment, the orifice is opened at the discoid superior portion of said support component, and the projection surrounding the orifice mouth may have the form of an hexagonal nut or of a Morse cone. Naturally, such projection or recess may have any adequate configuration, as long as it promotes a safe interlocking against mutual movement between the support component and a machined block received over the same. A possible configuration for this projection is characterized by having a staggered form, including a thin disc and superposed hexagonal nut of smaller external diameter.

Surprisingly, the invention achieved, for the first time, connection elements in a easy and fast way, at the dentist own office. Now the dentist will not have to acquire prefabricated connection elements. Additionally, the connection elements produced with the inventive supporting device are formed at his office, with characteristics already specifically adapted to the particularities of the locus where the prosthesis shall be positioned, so as to totally avoid the addition of substances or subtraction of material, as was the practice with the prior art.

BRIEF DESCRIPTION OF THE DRAWINGS

The supporting device for the manufacture of dental prosthetic components and, more particularly, of connecting elements, in accordance with the invention, shall be explained in greater detail in the following description, with basis in a preferred embodiment shown in the attached drawings, in which.

DETAILED DESCRIPTION OF A PREFERRED EMBODIMENT OF THE INVENTION

Figure 1:
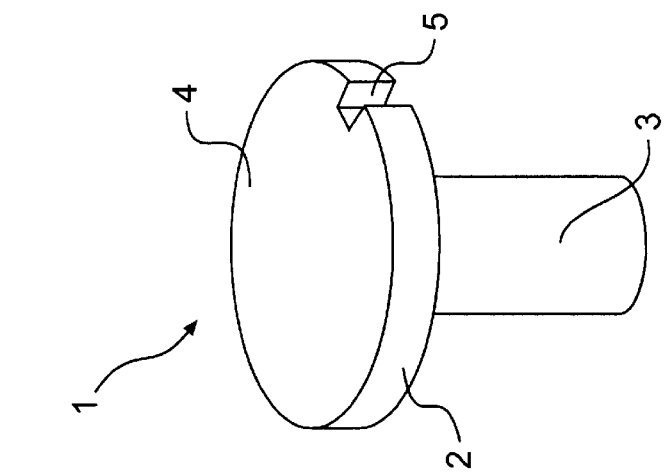
FIG. 1 is a perspective view of a support means for the manufacture of dental implants in accordance with the state of the art.

FIG. 1 shows a device for the manufacture of dental prosthetic components, more specifically, of blocks and crowns, in accordance with the state of the art. Such supporting device basically consists of a supporting component to receive a raw part to be sculpted or machined, made of a adequate material, such as ceramics, for the manufacture of a dental prosthesis.

The support component is generally referenced by number 1. The support component 1 is, generally, a one piece part consisting of a superior discoid portion 2 and a inferior shaft portion 3. The superior discoid portion 2 has a seating surface 4, a rift 5 having a certain radial extension, whose objective shall be described below. This support component 1 is generally fabricated from a adequate rigid material, being already known by those skilled in the art.

Figure 2:
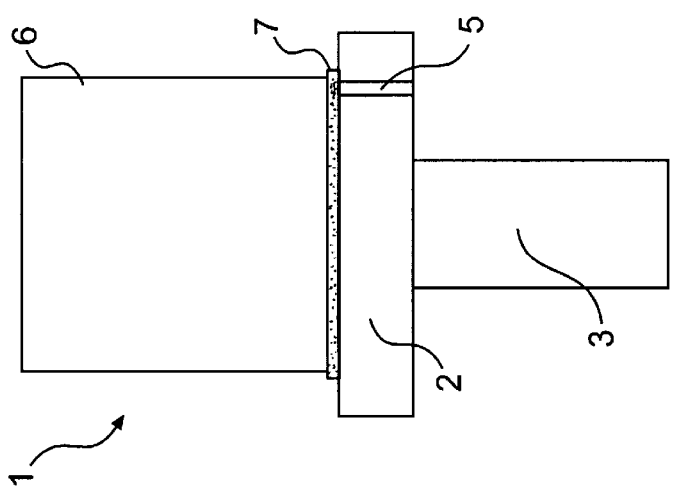
FIG. 2 shows the support means of FIG. 1, with a ceramic block adhered thereto.

FIG. 2 displays support component 1 of FIG. 1, having, on its seating surface 4, a ceramic block 6 adhered thereto for the manufacture of a dental prosthesis. As can be seen in this figure, the seating of ceramic block 6 on the seating surface 4 of support component 1 is achieved by the use of an adhesive, as is well known by those skilled in the odontology art.

Support component 1 with the ceramic block 6 is then taken to a prosthesis manufacturing or processing equipment. Said equipment includes, in general, a mold image capturing unit and a prosthesis machining or processing unit. The prosthesis machining or processing unit is provided with an rotary receptacle where support component 1 is positioned together with the ceramic block 6. Said support component 1 is positioned and locked on the rotary receptacle by means of a projection existing therein. The projection penetrates in the above mentioned radial rift 5 of the support component 1, so as to preclude rotation between the rotary receptacle and the support component, nonetheless permitting rotation of the assembly around the machining or processing unit driving axle. The assemblage locking is achieved through a radial screw positioned in the axle body. The unity is then turned on, rotating the assemblage.

The information regarding the cavity preparation are captured by means of a camera, an infrared camera when CEREC is used, and transmitted to the computer display where it will be processed by the operator, drafting over this image the format for the prosthesis to be manufactured. With this design information the computer will project informing to the machining unit the format for the prosthesis to be manufactured.

A prosthesis manufacturing or processing equipment can be, for example, the so-called CAD-CAM CEREC type, manufactured and supplied by Sirona. Evidently, there can also be used other similar equipment.

Figure 3:
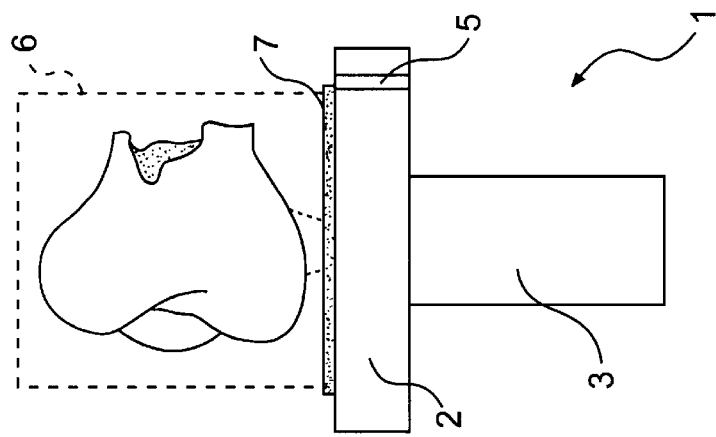
FIG. 3 shows the support means of FIG. 2, schematically showing the ceramic block, as well as an eventual crown already partially manufactured therefrom.

FIG. 3 displays the support component of FIG. 2, but with the ceramic block 6—shown in phantom—already processed or machined as a dental prosthesis, such as a dental crown. This machining or processing job may have been effected, for instance, by the above mentioned CAD-CAM CEREC equipment made by Sirona.

Figure 4:
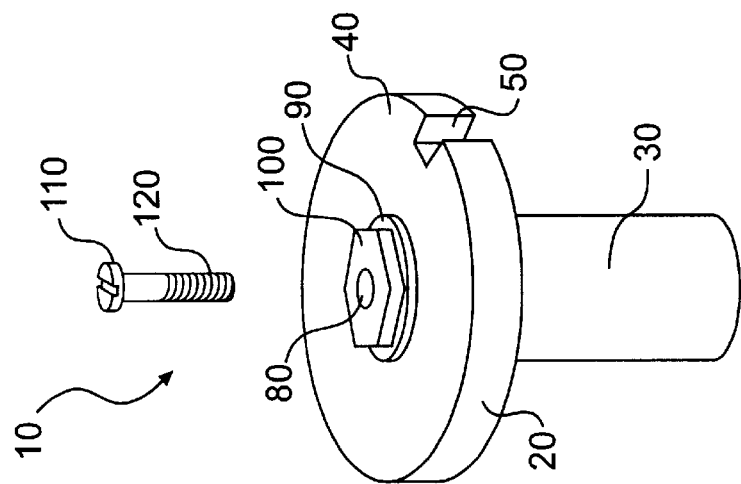
FIG. 4 is a perspective view of a support means for the manufacture of connection elements in accordance with the present invention.

FIG. 4 shows the new supporting device for the manufacture of connection elements components for dental implants, in accordance with the present invention. The reference numerals for those components similar to those of FIGS. 1 to 3 were used in the form of their tenths, so as to facilitate comparison.

In FIG. 4, the supporting device for the manufacture of connection elements components for dental prosthesis in accordance with the invention, in opposition to what was described in relation to FIGS. 1 to 3, does not exclusively serves to the manufacture of crowns, being more appropriate to the manufacture of connection elements, such as those used in dental implants.

In this preferred embodiment, the supporting device for the manufacture of dental implants, in accordance with the invention, includes a support component 10. It also includes a one piece support part including a discoid superior portion 20 and a inferior shaft portion 30. The discoid superior portion 20 has a seating surface 40 and can be provided with a radial rift 50, whose purpose was explained above with reference to FIGS. 1 to 3.

In accordance with the present invention, the discoid superior portion 20 has a central orifice 80 provided with an internal thread which extends along the geometric axis of the support component 10 formed by the discoid superior portion 20 and the inferior shaft portion 30. Central orifice 80 penetrates the discoid superior portion 20 and projects to a determined extension within the inferior shaft portion 30 so as that the seating surface 40 of said discoid superior portion 20 acquires the form of a circular crown.

In this preferred embodiment, the seating surface is configured with a anti-rotation device, which serves to prevent the mutual rotation between support component 10 and a machined block 60. This anti-rotation device has a staggered shape, i.e., an elevated portion configured as a thin disc 90 with a bigger diameter and a hexagonal nut 100 superimposed thereon and having a smaller external diameter. This configuration, with the machined block positioned on the seating surface 40 coupled in a corresponding recess in the machined block 40 (see FIG. 5) which is fixed by means of the locking screw 110, prevents the rotation between said components, allowing the rotation of the assemblage in a machining equipment.

Besides that, the supporting device 10 has a connection element in the forma of a head screw 110. Head screw 110 has a external thread portion 120, which couples to a corresponding internal thread portion of orifice 80.

Figure 5:
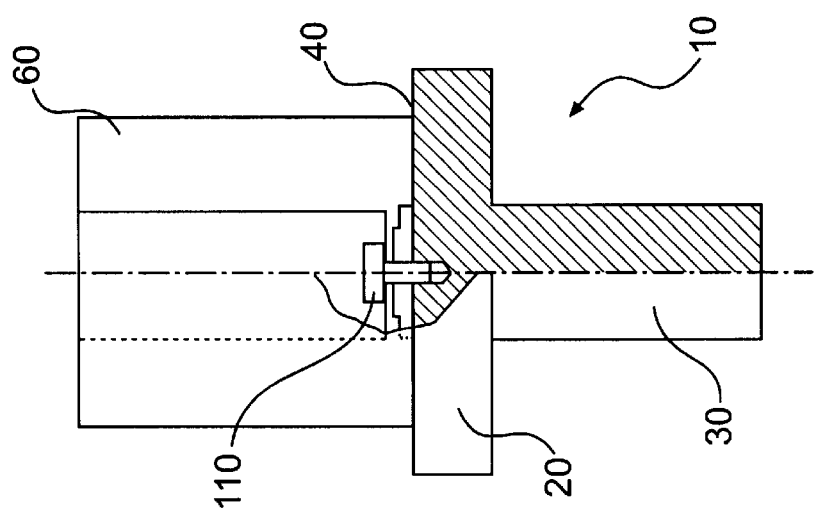
FIG. 5 is a side view of the support means of FIG. 4, with the machined block already cut, fixed thereto.

FIG. 5 displays another embodiment of the positioning for a machining block 60 for the manufacture of a connection element for the supporting device 10 in accordance with the invention. As can be seen, the machining block 60 must be initially provided with an orifice coincident or in line with the central orifice 80 of the support component 10 and positioned over the seating surface 40.

As mentioned above, the inferior surface of the machining block 60 couples, with its corresponding recess, to the staggered format of the seating surface 40 of support component 10, so as to prevent mutual rotation between said components. The screw shaft 10 is then inserted within the corresponding orifice of machining block and is locked by the cooperation between the external threaded portion 120 of screw 110 and the internal threaded portion of orifice 80, so as to provide a firm interlocking of ceramic block or any other material adequate to be processed or machined. Finally, the assembly is positioned in a machining equipment for the manufacture of a connection element.

Figure 6:
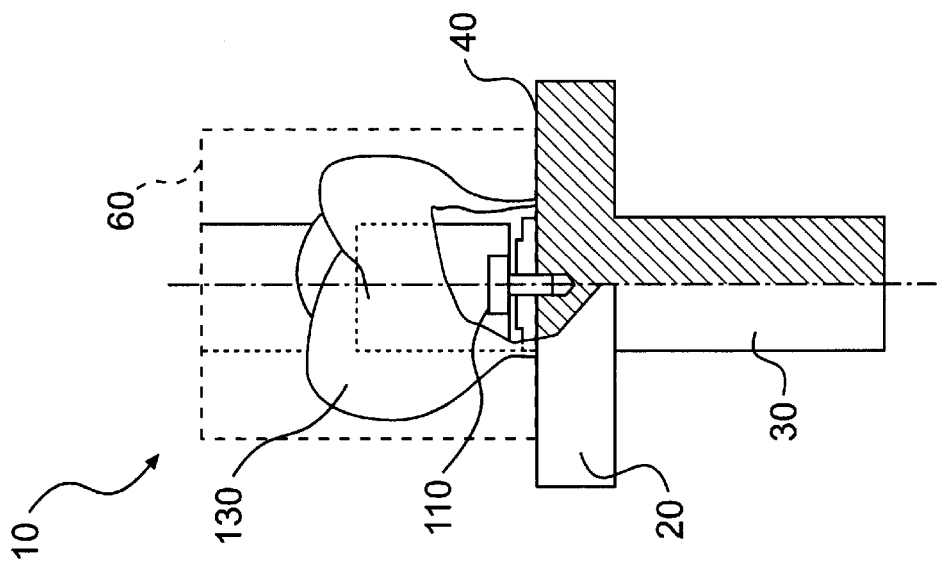
FIG. 6 is a schematic side view of the support means in accordance with the invention, showing a prosthesis already machined from the machined block of FIG. 5.

FIG. 6 shows the inventive supporting device, similar to that of FIG. 5, but already with the finished connection element, which was produced from the machining block 110.

As can be seen in this figure, the prosthesis 130 is machined or processed to its finished condition to be positioned on its definitive place, i.e., on the implanted part. This is made possible by the fact that the inferior surface of the block presents a recess whose form corresponds to that of the similar projection of the superior portion of the implanted part. By this artifice additional molding work is made redundant, as the prosthesis couples perfectly to the implanted part, without any further manual machining.

With the supporting device configuration of the present invention, it is possible to manufacture connection elements from any material for dental implants at an extremely low cost and at the dentist own office.

While the invention has been described with basis on a preferred embodiment, it is clear that many alternatives, modifications and variations will be obvious to those skilled in the art. Therefore, it shall be considered that all these alternatives, modifications and variations are included within the spirit and scope of the attached claims.

What is claimed is:

1. A supporting device for the manufacture of dental prosthetic components including connecting elements, the supporting device comprising:

a support component having a seating surface at one end of a shaft portion defining a longitudinal axis, and an orifice extending along the longitudinal axis and opening through the seating surface;

a first coupling structure in the orifice: and a fastening element receivable in the orifice and having a second coupling structure cooperable with the first coupling structure to releasably secure the fastening element to the support component.

2. The supporting device of claim 1, wherein the fastening element is a head screw.

3. The supporting device of claim 2, wherein the first coupling structure comprises an internal thread within the orifice, and the second coupling structure comprises an external threaded shaft portion of the head screw.

4. A supporting device for the manufacture of dental prosthetic components including connecting elements, the supporting device comprising:

a support component having a single rotationally symmetrical part having a substantially discoid superior portion, an inferior shaft portion having a longitudinal axis, and an orifice extending along the longitudinal axis, a first coupling structure in the orifice: and a fastening element receivable in the orifice and having a second coupling structure cooperable with the first coupling structure to releasably secure the fastening element to the support component.

5. The supporting device of claim 4, wherein the orifice opens through discoid superior portion.

6. The supporting device of claim 4, wherein the discoid superior portion has a seating surface and comprises an antirotation formation surrounding an open end of the orifice.

7. The supporting device of claim 6, wherein the antirotation formation comprises a hexagonal nut surrounding the open end of the orifice.

8. The supporting device of claim 6, wherein the projection has a staggered form including a thin disc and a smaller external diameter hexagonal nut over the thin disc.

9. A method of making connecting elements for dental implants, comprising:

mounting a machining block on a seating surface of a support having a shaft portion with an axial orifice opening through the seating surface, by inserting a removable fastening element through the machining block and into the orifice;

placing the mounted machining block and support into a machining unit;

shaping the machining block; and removing the shaped machining block for mounting on an implant.

10. The method of claim 9, wherein the seating surface and axial orifice on the support are substantially the same as a corresponding seating surface and axial orifice on the implant.

* * * * *